US008298785B2

(12) United States Patent
Coffey

(10) Patent No.: US 8,298,785 B2
(45) Date of Patent: Oct. 30, 2012

(54) USE OF RIBOZYMES IN THE DETECTION OF ADVENTITIOUS AGENTS

(75) Inventor: Matthew C. Coffey, Calgary (CA)

(73) Assignee: Oncolytics Biotech Inc., Calgary, Alberta (CA)

(*) Notice: Subject to any disclaimer, the term of this patent is extended or adjusted under 35 U.S.C. 154(b) by 333 days.

(21) Appl. No.: 12/707,307

(22) Filed: Feb. 17, 2010

(65) Prior Publication Data
US 2010/0143892 A1 Jun. 10, 2010

Related U.S. Application Data

(63) Continuation of application No. 10/375,700, filed on Feb. 26, 2003, now abandoned.

(60) Provisional application No. 60/441,760, filed on Jan. 23, 2003, provisional application No. 60/360,730, filed on Feb. 28, 2002.

(51) Int. Cl.
C12Q 1/22 (2006.01)
C12Q 1/68 (2006.01)
C12P 19/34 (2006.01)
A01N 43/04 (2006.01)
C07H 21/02 (2006.01)

(52) U.S. Cl. ......... 435/31; 435/6; 435/91.1; 435/91.31; 514/44; 536/23.1; 536/24.32; 536/24.5

(58) Field of Classification Search ............. 435/6, 91.1, 435/91.31, 455, 31; 424/9.2; 536/23.1, 24.5, 536/24.32; 514/44
See application file for complete search history.

(56) References Cited

U.S. PATENT DOCUMENTS

| 4,987,071 | A | 1/1991 | Cech et al. |
| 5,168,053 | A | 12/1992 | Altman et al. |
| 5,254,678 | A | 10/1993 | Haseloff et al. |
| 5,631,115 | A | 5/1997 | Ohtsuka et al. |
| 5,631,359 | A | 5/1997 | Chowrira et al. |
| 5,670,361 | A | 9/1997 | Wong-Staal et al. |
| 5,693,532 | A | 12/1997 | McSwiggen et al. |
| 5,972,704 | A | 10/1999 | Draper et al. |
| 6,107,028 | A | 8/2000 | Kay et al. |
| 6,110,461 | A | 8/2000 | Lee et al. |
| 6,136,307 | A | 10/2000 | Lee et al. |
| 6,307,041 | B1 | 10/2001 | Ruffner et al. |

FOREIGN PATENT DOCUMENTS

| EP | 0 360 257 | 3/1990 |
| EP | 1 032 269 | 4/1999 |
| NZ | 227332 | 8/1991 |
| NZ | 235789 | 7/1992 |
| WO | WO 91/04319 | 4/1991 |
| WO | WO 91/04324 | 4/1991 |
| WO | WO 94/13791 | 6/1994 |
| WO | WO 94/18992 | 9/1994 |
| WO | WO 94/25627 | 11/1994 |
| WO | WO 95/10608 | 4/1995 |
| WO | WO 99/08692 | 2/1999 |
| WO | WO 99/18799 | 4/1999 |
| WO | WO 00/24912 | 5/2000 |
| WO | WO 01/72964 | 10/2001 |
| WO | WO 02/12435 | 2/2002 |
| WO | WO 02/095042 | 11/2002 |

OTHER PUBLICATIONS

Strong et al., EMBO, vol. 17, No. 12, pp. 3351-3362 (1998).*
Shahi et al, Proc. Nat'l. Acad. Sci., vol. 98, No. 7, pp. 4101-4106 (2002).*
Andreansky, S.A., et al., "The application of genetically engineered herpes simplex viruses to the treatment of experimental brain tumors", (1996), Proc. Natl. Acad. Sci 93(21):11313-11318.
Bar-Eli, N., et al., "Preferential Cytotoxic Effect of Newcastle Disease Virus on Lymphoma Cells," J. Cancer Res. Clin. Oncol., (1996),122: 409-415.
Bergmann, M., et al., "A genetically engineered influenza A virus with ras-dependent oncoloytic properties," Cancer Res., (2001), 61:8188-8193.
Bischoff Jr. et al., "An Adenovirus Mutant that Replicates Selectively in p53-Deficient Human Tumor", Science, (1996), 274(5286):373-376.
Blagoslelonny, M.V., et al., "In vitro Evaluatin of a p53-Expressing Adenovirus as an Anti-Cancer Drug," Int. J. Cancer, (1996), 67(3):386-392.
Chandron and Nibert, "Protease cleavage of reovirus capsid protein mul and muiC is blocked by alkyl sulfate detergents, yielding a new type of infectious subvirion particle", J. of Virology, (1998), 72(1):467-75 (1998).
Chang et al., "Identification of a Conserved Motif that is Necessary for Binding the Caccina Virus E3L Gene Products to Double-Stranded RNA," Virol., (1993), 194:537-547.
Chang et al., "Rescur of Vaccina Virus Lacking the E3L Gene by Mutants of E3L," J. Virol., (1995), 69:6605-6608.
Chang et al., "The E3L gene of vaccine virus encodes an inhibitor of the interferon-induced, double-stranded RNA-dependent protein kinase," Proc. Natl. Acad. Sci., (1992), 89:4825-4829.
Coffey, M.C., et al., "Reovirus therapy of tumors with activated Ras pathway", Science, (1998), 282: 1332-1334.
Duncan et al., "Conformational and functional analysis of the C-terminal globular head of the reovirus cell attachment protein", Virology, (1991), 182(2):810-9.

(Continued)

Primary Examiner — Jane Zara
(74) Attorney, Agent, or Firm — McKeon, Meunier, Carlin & Curfman, LLC

(57) ABSTRACT

The present invention provides a method of detecting adventitious agents in a composition comprising a microorganism by using ribozyme-expressing indicator cells, as well as indicator cells useful in such detection.

10 Claims, No Drawings

OTHER PUBLICATIONS

Farassati, F., et al., "Oncogenes in Ras signalling pathway dictate host-cell permissiveness to herpes simplex virus 1", *Nat. Cell Biol.*, (2001), 3(8):745-750 (2001).

Fields, B.N. et al., *Fundamental Virology (3rd Edition)*, Lippincott-Raven (1996).

Fueyo, J., et al., "A Mutant Oncolytic Adenovirus Targeting the Rb Pathway Produces Anti-Glioma Effect in Vivo", *Oncogene*, (2000), 19(1):2-12.

Heise, C. et al., "Replication-selective adenoviruses as oncolytic agents", *J. Clin. Invest.*, (2000), 105(7):847-51.

Kawagishi-Kobayashi, M. et al., "Regulation of the Protein Kinase PKR by the VAccinia Virus Pseudosubstrate Inhibitor K3L is Dependent on Residues Conserved between the K3L Protein and the PKR Substrate α," *Mol. Cell. Biol.*, (1997), 17:4146-4158.

Maeda, A., et al., "Inhibition of viral multiplication in acute and chronic stages of infection by ribozymes targeted against the polymerase gene of mouse hepatitis virus." *Corona- and Related Viruses* (1995), pp. 399-404.

Mah et al., "The N-terminal quarter of reovirus cell attachment protein sigma 1 possesses intrinsic virion-anchoring function", *Virology*, (1990), 179(1):95-103.

Nemunaitis, J., "Oncolytic viruses," *Invest. New Drugs*, (1999), 17:375-386.

Nibert, M.L., Schiff, L.A., and Fields, B.N., "Reoviruses and their replication", *Fundamental Virology* (Fields et al., *3rd Edition*), Lippencott-Raven Press, (1996), pp. 1557-1596.

Oberhaus, S., et al., "Reovirus Infection and Tissue Injury in the Mouse Central Nervous System Are Associted with Apoptosis," *Journal of Virology*, (1997), 71(3):2100-2106.

Pastan and Gottesman, "Multidrug resistance", *Annu. Rev. Med.*, (1991), 42: 277-286.

Pyle, A. M., "Ribozymes: a distinct class of metalloenzymes", *Science*, (1993), 261, 709-714.

Reichard, K.W., et al., "Newcastle Disease Virus Selectively Kills Human Tumor Cells", *J. of Surgical Research*, (1992), 52:448-453.

Romano et al., "Inhibitition of Double-Stranded RNA-Dependent Protein Kinase PKR by Vaccina Virus E3: Role of Complex Formation and the E3 N-Terminal Domain," *Mol. Cell. Bio.*, (1998), 18(12):7304-7316.

Sambrook and Russell, *Molecular Cloning (3rd Ed.)*, CSHL Press, New York (2001).

Shahi, S. et al., "Ribozymes that cleave reovirus genome segment Si also protect cells from pathogenesis caused by reovirus infection", *Proc. Natl. Acad. Sci. USA*, (2001), 98:4104-4106.

Shahi, S., et al., "Multitarget ribozyme against the S1 genome segment of reovirus possesses novel cleavage activities and is more efficacious than its constituent mono-ribozymes." *Antiviral Research* (2002), vol. 55(1):129-140.

Sharp et al., "The Vaccina Virus E3L Gene Product Interacts with both the Regulatory and the Substrate Binding Regions of PKR: Implications for PKR Autoregulation," *Virology*, (1998), 250:302-315.

Smith et al., "Polypeptide components of virions, top component and cores of reovirus type 3" *Virology* 39:791-810 (1969).

Stojdl, D.F., et al., "Exploiting Tumor-Specific Defects in the Interferon Pathway with a Previously Unknown Oncolytic Virus", Nat. Med., (2000), 6(7):821-825.

Strong, J.E. and P.W. Lee, "The v-erbV oncogene confers enhanced cellular susceptibility to reovirus infection", *J. Virol.*, (1996), 70: 612-616.

Strong, J.E., et al., "Evidence that the Epidermal Growth Factor Receptor on Host Cells Confers Reovirus Infection Efficiency", *Virology*, (1993), 197(1): 405-411.

Turner and Duncan, "Site directed mutagenesis of the C-terminal portion of reovirus protein sigma 1: evidence for a conformation-dependent receptor binding domain", *Virology*, (1992), 186(1):219-227.

Weinberg, M., et al., "Hammerhead ribozyme-mediated inhibition of hepatitis B virus X gene express in cultured cells." *Journal of Hepatology* (2000), vol. 33:142-151.

Yoon, S.S., et al., "An Oncolytic Herpes Simplex Virus Type I Selectively Destroys Diffuse Liver Metastases from Colon Carcinoma", *FASEB*, (2000), J. 14:301-311.

Zaug, A.J. and Cech, T.R., "The intervening sequence RNA of Tetrahymena is an enzyme", *Science*, (1986), 231:470-475.

Zorn, U. et al., "Induction of Cytokines and Cytotoxicity against Tumor Cells by Newcastle Disease Virus", *Cancer Biotherapy*, (1994), 9(3):22-235.

* cited by examiner

USE OF RIBOZYMES IN THE DETECTION OF ADVENTITIOUS AGENTS

RELATED APPLICATIONS

This application is a continuation application of U.S. Ser. No. 10/375,700, filed Feb. 26, 2003, which claims the benefit of U.S. Provisional Application Ser. No. 60/360,730, filed Feb. 28, 2002; and Ser. No. 60/441,760, filed Jan. 23, 2003. The entire disclosure of these prior applications is hereby incorporated by reference.

FIELD OF THE INVENTION

This invention relates to a method of detecting adventitious agents in a composition comprising a microorganism, as well as indicator cells useful in such detection.

REFERENCES

U.S. Pat. No. 6,307,041.
U.S. Pat. No. 6,136,307.
U.S. Pat. No. 5,631,359.
U.S. Pat. No. 5,631,115.
U.S. Pat. No. 5,254,678.
U.S. Pat. No. 5,168,053.
U.S. Pat. No. 4,987,071.
WO 91/04319.
WO 91/04324.
WO 94/18992.
WO 94/25627.
WO 99/18799.
WO 02/095042.
European Application No. 89 117 424.
Andreansky, S. A., et al., "The application of genetically engineered herpes simplex viruses to the treatment of experimental brain tumors", *Proc. Natl. Acad. Sci.* 93 (21): 11313-11318 (1996).
Bar-Eli, N., et al., "preferential cytotoxic effect of Newcastle disease virus on lymphoma cells", *J. Cancer Res. Clin. Oncol.* 122: 409-415 (1996).
Bergmann, M., et al., "A genetically engineered influenza A virus with ras-dependent oncolytic properties", *Cancer Res.* 61:8188-8193 (2001).
Bischoff J R. et al., "An Adenovirus Mutant that Replicates Selectively in p53-Deficient Human Tumor", *Science* 274 (5286):373-6 (1996).
Blagoslelonny, M. V., et al., "in vitro Evaluation of a p53-Expressing Adenovirus as an Anti-Cancer Drug", *Int. J. Cancer* 67 (3):386-392 (1996).
Chandron and Nibert, "Protease cleavage of reovirus capsid protein mu1 and mu1C is blocked by alkyl sulfate detergents, yielding a new type of infectious subvirion particle", *J. of Virology* 72 (1):467-75 (1998).
Chang et al., *J. Virol.* 69:6605-6608 (1995).
Chang et al., *Proc. Natl. Acad. Sci.* 89:4825-4829 (1992).
Chang et al., *Virol.* 194:537-547 (1993).
Coffey, M. C., et al., "Reovirus therapy of tumors with activated Ras pathway", *Science* 282: 1332-1334 (1998).
Duncan et al., "Conformational and functional analysis of the C-terminal globular head of the reovirus cell attachment protein", *Virology* 182 (2):810-9 (1991).
Farassati, F., et al., "Oncogenes in Ras signaling pathway dictate host-cell permissiveness to herpes simplex virus 1", *Nat. Cell Biol.* 3 (8):745-750 (2001).
Fields, B. N. et al., *Fundamental Virology* (3rd Edition), Lippincott-Raven (1996).
Fueyo, J., et al., "A Mutant Oncolytic Adenovirus Targeting the Rb Pathway Produces Anti-Glioma Effect in Vivo", *Oncogene* 19 (1):2-12 (2000).
Heise, C. et al., "Replication-selective adenoviruses as oncolytic agents", *J. Clin. Invest.* 105 (7):847-51 (2000).
Kawagishi-Kobayashi, M. et al., *Mol. Cell. Biol.* 17:4146-4158 (1997).
Mah et al., "The N-terminal quarter of reovirus cell attachment protein sigma 1 possesses intrinsic virion-anchoring function", *Virology* 179 (1):95-103 (1990).
Nemunaitis, J., *Invest. New Drugs* 17:375-386 (1999).
Nibert, M. L., Schiff, L. A., and Fields, B. N., "Reoviruses and their replication", pages 1557-96 in *Fundamental Virology* (Fields et al., 3rd Edition), Lippencott-Raven Press, 1996.
Pastan and Gottesman, "Multidrug resistance", *Annu. Rev. Med.* 42: 277-286 (1991).
Pyle, A. M., "Ribozymes: a distinct class of metalloenzymes", Science 261, 709-714 (1993).
Reichard, K. W., et al., "Newcastle Disease Virus Selectively Kills Human Tumor Cells", *J. of Surgical Research* 52:448-453 (1992).
Romano et al., *Mol. Cell. Bio.* 18 (12):7304-7316 (1998).
Sambrook and Russell, *Molecular Cloning* ($3^{rd}$ Ed.), CSHL Press, New York (2001).
Shahi, S. et al., "Ribozymes that cleave reovirus genome segment S1 also protect cells from pathogenesis caused by reovirus infection", *Proc. Natl. Acad. Sci. USA* 98:4104-4106 (2001).
Sharp et al., *Virology* 250:302-315 (1998).
Stojdl, D. F., et al., "Exploiting Tumor-Specific Defects in the Interferon Pathway with a Previously Unknown Oncolytic Virus", *Nat. Med.* 6 (7):821-825 (2000).
Strong, J. E. and P. W. Lee, "The v-erbV oncogene confers enhanced cellular susceptibility to reovirus infection", *J. Virol.* 70: 612-616 (1996).
Strong, J. E., et al., "Evidence that the Epidermal Growth Factor Receptor on Host Cells Confers Reovirus Infection Efficiency", *Virology* 197 (1): 405-411 (1993).
Turner and Duncan, "Site directed mutagenesis of the C-terminal portion of reovirus protein sigma1: evidence for a conformation-dependent receptor binding domain", *Virology* 186 (1):219-27 (1992).
Yoon, S. S., et al., "An Oncolytic Herpes Simplex Virus Type I Selectively Destroys Diffuse Liver Metastases from Colon Carcinoma", *FASEB J.* 14:301-311 (2000).
Zaug, A. J. and Cech, T. R., "The intervening sequence RNA of *Tetrahymena* is an enzyme", Science 231:470-475 (1986).
Zorn, U. et al., "Induction of Cytokines and Cytotoxicity against Tumor Cells by Newcastle Disease Virus", *Cancer Biotherapy* 9 (3):22-235 (1994).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

In the field of medical or biological sciences, there has always been the demand to produce large quantities of microorganisms such as viruses, bacteria, yeasts, other fungi, parasites and prions. The resulting microorganisms can be used to isolate and purify microbial proteins, generate vaccines, or provide infectious microorganisms for laboratory or medical studies. Recently, the new development of virus therapy has further necessitated the need for efficient production of infectious viruses.

Reovirus therapy (U.S. Pat. No. 6,136,307) is an example of virus therapy. Reovirus is a double-stranded RNA virus with a segmented genome. The receptor for the mammalian reovirus is a ubiquitous molecule, therefore reovirus is capable of binding to a multitude of cells. However, most cells are not susceptible to reovirus infection and binding of reovirus to its cellular receptor results in no viral replication or virus particle production. This is probably the reason why reovirus is not known to be associated with any particular disease.

It was discovered recently that cells transformed with the ras oncogene become susceptible to reovirus infection, while their untransformed counterparts are not (Strong et al., 1998). For example, when reovirus-resistant NIH 3T3 cells were transformed with activated Ras or Sos, a protein which activates Ras, reovirus infection was enhanced. Similarly, mouse fibroblasts that are resistant to reovirus infection became susceptible after transfection with the EGF receptor gene or the v-erbB oncogene, both of which activate the ras pathway (Strong et al., 1993; Strong et al., 1996). Thus, reovirus can selectively infect and kill cells with an activated ras pathway.

Ras pathway activation accounts for a large percentage of mammalian tumors. Activating mutations of the ras gene itself occur in about 30% of all human tumors (Bos, 1989), primarily in pancreatic (90%), sporadic colorectal (50%) and lung (40%) carcinomas, as well as myeloid leukemia (30%). Activation of factors upstream or downstream of ras in the ras pathway is also associated with tumors. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain. Accordingly, reovirus therapy, which is highly selective for ras-associated tumor cells, can be used to treat a vast variety of tumors.

Reovirus can be produced and purified in bulk preparations (U.S. Patent Application Publication Number 2002/0037576 A1). To ensure that the reovirus preparation does not contain adventitious agents which may result in undesired side effects, the preparation is validated by using a susceptible cell line and anti-reovirus antibodies. Thus, the cell line is exposed to either the virus preparation alone, or the virus preparation that has been neutralized by a reovirus-specific neutralizing antibody. If the antibody neutralized virus preparation is still pathogenic to the cell line, the virus preparation must contain an adventitious virus or other organism. The preparation is then discarded or further purified.

This validating protocol is expensive, as it requires large amounts of high affinity, high titer antibodies to neutralize the virus. This problem is further exacerbated now that we can produce reovirus very efficiently, and the requirement for antibody is even higher. Therefore, a more cost effective approach is desirable.

SUMMARY OF THE INVENTION

The present invention provides a method of validating microbial preparations using a ribozyme that is specific for the microorganism being prepared. For example, a plasmid encoding a ribozyme that specifically cleaves the genome of reovirus can be introduced into cells that are susceptible to reovirus infection. The transfected cells, by expressing the ribozyme, are capable of inactivating reovirus and thus will not be infected by the virus. The ribozyme-expressing cells are then subjected to a reovirus preparation, and any pathogenic effects caused by the reovirus preparation will indicate that an adventitious agent is present in the reovirus preparation. Conversely, the absence of any pathogenic effect validates the preparation as having no detectable adventitious agents.

This method is also applicable to viruses or other microorganisms having a DNA genome. Since the DNA genome must be transcribed into RNA for successful infection by the microorganism, a ribozyme specific for the RNA transcript will inhibit infection as well as replication of the microorganism. Again, if the ribozyme-expressing cells show any pathogenic effects due to the microbial preparation, an adventitious agent must be present in the preparation. Similarly, this method can be used to validate preparations of prions as well.

Accordingly, the present invention provides a method of detecting the presence of an adventitious agent in a composition comprising a reovirus, comprising:

(a) providing a population of indicator cells that expresses a ribozyme, wherein the ribozyme is capable of specifically cleaving the genome of the reovirus;

(b) contacting the indicator cells with the composition under conditions that allow for cleavage of the genome of the reovirus by the ribozyme; and (c) determining the effect of the composition on the indicator cells, wherein any pathogenic effect indicates the presence of an adventitious agent in the composition in addition to the reovirus.

The cells may express the ribozyme transiently or permanently. Preferably, the cells comprise a ribozyme-encoding gene that is integrated into the genome of the cells. The ribozyme may cleave any part of the reovirus genome that is important for replication or infection by reovirus. For example, the ribozyme may cleave the S1 segment of reovirus, such as Rz-553 or Rz-984.

This method can be used to detect adventitious agents in any reovirus. The reovirus is preferably a mammalian reovirus, more preferably a serotype 3 reovirus, and most preferably a Dearing strain reovirus. The reovirus may be a recombinant reovirus. The recombinant reovirus may be generated by co-infection of mammalian cells with different subtypes of reovirus. The recombinant reovirus may be naturally-occurring or non-naturally-occurring. The recombinant reovirus may be from two or more strains of reovirus, particularly two or more strains of reovirus selected from the group consisting of strain Dearing, strain Abney, strain Jones, and strain Lang. The recombinant reovirus may also result from reassortment of reoviruses from different serotypes, such as selected from the group consisting of serotype 1 reovirus, serotype 2 reovirus and serotype 3 reovirus. The recombinant reovirus may comprise naturally-occurring variant coat protein coding sequences or mutated coat protein coding sequences.

The present invention can be applied to compositions of any microorganism, including any virus. Accordingly, the present invention provides a method of detecting the presence of an adventitious agent in a composition comprising a virus wherein the virus contains an RNA genome or utilizes an RNA transcript to replicate, comprising:

(a) providing a population of indicator cells that expresses a ribozyme, wherein the ribozyme is capable of specifically cleaving the RNA genome or RNA transcript of the virus;

(b) contacting the indicator cells with the composition under conditions that allow for cleavage of the RNA genome or RNA transcript of the virus by the ribozyme; and (c) determining the effect of the composition on the indicator cells, wherein any pathogenic effect indicates the presence of an adventitious agent in the composition in addition to the virus.

The cells may express the ribozyme transiently or permanently. Preferably, the cells comprise a ribozyme-encoding gene that is integrated into the genome of the cells.

The virus may be a DNA virus or RNA virus. Preferably, the virus is an oncolytic virus, which is capable of selectively replicating in neoplastic cells. Preferred oncolytic viruses include, but are not limited to, modified adenovirus, modified HSV, modified vaccinia virus, modified parapoxvirus orf virus, modified influenza virus, p53-expressing viruses, the ONYX-015 virus, the Delta24 virus, and vesicular stomatitis virus.

Another aspect of the present invention provides a method of validating a composition comprising a microorganism, comprising:

(a) providing a population of indicator cells that expresses a ribozyme, wherein the ribozyme is capable of specifically cleaving the RNA genome or RNA transcript of the microorganism to inhibit replication or infection of the microorganism;

(b) contacting the indicator cells with the composition under conditions that allow for cleavage of the RNA genome or RNA transcript of the microorganism by the ribozyme; and (c) determining the effect of the composition on the indicator cells, wherein the absence of any pathogenic effect validates the composition as having no detectable adventitious agent.

The microorganism is preferably a virus, more preferably a virus capable of selectively replicating in neoplastic cells, and most preferably a reovirus.

Another aspect of the present invention provides an indicator cell useful for detecting an adventitious agent in a composition of microorganism wherein the indicator cell permanently expresses a ribozyme that is capable of cleaving the genome or RNA transcript of the microorganism. Preferably, a gene coding for the ribozyme is integrated into the genome of the indicator cell. The microorganism is preferably a virus and more preferably a reovirus. The cell is preferably derived from the human embryonic kidney 293 cells (HEK 293 cells).

DETAILED DESCRIPTION OF THE INVENTION

The present invention provides a method of detecting adventitious agents in a preparation of a microorganism by using a ribozyme that is specific for the microorganism. Thus, a cell population susceptible to the microorganism is transfected by an expressing vector encoding the ribozyme and exposed to the composition comprising the microorganism. Infection and/or replication of the microorganism in the cells are inhibited by the ribozyme. Therefore, the microorganism does not cause any pathogenic effect on the cells. As a result, any sign of pathogenic effect is indicative of the presence of an adventitious agent in the microorganism preparation.

Prior to describing the invention in further detail, the terms used in this application are defined as follows unless otherwise indicated.

Definitions

An "adventitious agent" is an agent that is not intended to be included in a composition. Preferably, an adventitious agent is an infectious agent, namely an agent capable of infecting a cell.

"Infecting" a cell refers to the act of entering into and replicating in a cell.

A "ribozyme" is an RNA molecule or RNA derivative that is capable of catalytically cleaving another RNA (the "target RNA"). The ribozymes of the present invention may have the characteristics of naturally occurring ribozymes. For example, the ribozymes isolated from *Tetrahymena thermophila* has an eight base pair active site which hybridizes to a target RNA sequence before cleaving the target (see, for example, Zaug and Cech, 1986). Free guanosine or guanosine derivatives is required for this reaction, and a guanosine is added to the 5' end of cleaved RNA. The ribozymes of the present invention may also be synthetic ribozymes, such as those described in U.S. Pat. No. 5,254,678. These synthetic ribozymes have separate hybridizing regions and catalytic regions; therefore, the hybridizing regions can be designed to recognize any target sequences. In addition, the cleaved RNA is not modified by these ribozymes.

An "indicator cell" is a cell that expresses a ribozyme, which ribozyme is capable of cleaving and inactivating a microorganism to be validated. The indicator cell, when not expressing the ribozyme, is susceptible to infection of the microorganism.

A "pathogenic effect" is an adverse effect on the growth or maintenance of a cell, particularly the effects associated with microbial infections. Pathogenic effects include, but are not limited to, cytopathic effect (CPE), cell rupture, inhibition of growth, inhibition of protein synthesis, and apoptosis.

"Cytopathic effect" is an observable change in cell structure. Cytopathic effect may vary with cell types and cause of death, and can be determined according to established knowledge in the art. For example, some of the most common effects of viral infection are morphological changes such as (a) cell rounding and detachment from the substrate; (b) cell lysis; (c) syncytium formation; and (d) inclusion body formation. Cytopathic effect shown by reovirus-infected cells, for instance, is indicated by the cells becoming swollen and granular in appearance and the cell clumps breaking up.

"Validating" a composition, as used herein, means proving that the composition does not contain an adventitious agent that is detectable by the method employed.

"Reovirus" refers to any virus classified in the reovirus genus, whether naturally occurring, modified or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998). For example, the virion may be treated with chymotrypsin in the presence of micelle forming concentrations of alkyl sulfate detergents to generate a new infectious subvirion particle.

The reovirus may be a recombinant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses (Nibert et al. 1995).

Accordingly, the invention contemplates the recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the recombinant reovirus that has undergone recombination in the presence of chemical mutagens, including but not limited to dimethyl sulfate and ethidium bromide, or physical mutagens, including but not limited to ultraviolet light and other forms of radiation.

The invention further contemplates recombinant reoviruses that comprise deletions or duplications in one or more genome segments, that comprise additional genetic information as a result of recombination with a host cell genome, or that comprise synthetic genes.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, 1992; Duncan et al., 1991; Mah et al., 1990).

The reovirus is preferably a reovirus modified to reduce or eliminate an immune reaction to the reovirus. Such modified reovirus are termed "immunoprotected reovirus". Such modifications could include packaging of the reovirus in a liposome, a micelle or other vehicle to mask the reovirus from the mammals immune system. Alternatively, the outer capsid of the reovirus virion particle may be removed since the proteins present in the outer capsid are the major determinant of the host humoral and cellular responses.

A "neoplastic cell", also known as a "cell with a proliferative disorder", refers to a cell which proliferates at an abnormally high rate. A new growth comprising neoplastic cells is a neoplasm, also known as a tumor. A neoplasm is an abnormal tissue growth, generally forming a distinct mass, that grows by cellular proliferation more rapidly than normal tissue growth. A neoplasm may show partial or total lack of structural organization and functional coordination with normal tissue. As used herein, a neoplasm is intended to encompass hematopoietic tumors as well as solid tumors.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

"Ras-activated neoplastic cells" or "ras-mediated neoplastic cells" refer to cells which proliferate at an abnormally high rate due to, at least in part, activation of the ras pathway. The ras pathway may be activated by way of ras gene structural mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or sos results in activation of the ras pathway. Ras-mediated neoplastic cells include, but are not limited to, ras-mediated cancer cells, which are cells proliferating in a malignant manner due to activation of the ras pathway.

An "oncolytic" virus is a virus that is capable of selectively infecting and killing neoplastic cells. In particular, the oncolytic virus is capable of selectively replicating in and lysing neoplastic cells. Examples of oncolytic viruses include, but are not limited to, modified adenovirus, modified HSV, modified vaccinia virus, modified parapoxvirus orf virus, modified influenza virus, p53-expressing viruses, the ONYX-015 virus, the Delta24 virus, vesicular stomatitis virus, the herpes simplex virus 1 mutant which is defective in hrR3, Newcastle disease virus, encephalitis virus, herpes zoster virus, hepatitis virus, influenza virus, varicella virus, and measles virus.

The term "attenuated adenovirus" or "modified adenovirus" means an adenovirus in which the gene product or products which prevents the activation of PKR is lacking, inhibited or mutated such that PKR activation is not blocked. Preferably, the VAI RNA's are not transcribed. Such attenuated or modified adenovirus would not be able to replicate in normal cells that do not have an activated ras pathway, however, it would be able to infect and replicate in cells having an activated ras pathway.

The term "attenuated HSV" or "modified HSV" means a herpes simplex virus (HSV) in which the gene product or products that prevents the activation of PKR is lacking, inhibited or mutated such that PKR activation is not blocked. Preferably, the HSV gene $_{65}$ ɣ34.5 is not transcribed. Such attenuated or modified HSV would not be able to replicate in normal cells that do not have an activated ras pathway, however, it would be able to infect and replicate in cells having an activated ras pathway.

"Parapoxvirus orf virus" is a poxvirus. It is a virus that induces acute cutaneous lesions in different mammalian species, including humans. Parapoxvirus orf virus naturally infects sheep, goats and humans through broken or damaged skin, replicates in regenerating epidermal cells and induces pustular lesions that turn to scabs (Haig et al., 1998). The term "attenuated parapoxvirus orf virus" or "modified parapoxvirus orf virus" means a parapoxvirus orf virus in which the gene product or products which prevents the activation of PKR is lacking, inhibited or mutated such that PKR activation is not blocked. Preferably, the gene OV20.0L is not transcribed. Such attenuated or modified parapoxvirus orf virus would not be able to replicate in normal cells that do not have an activated ras pathway, however, it would be able to infect and replicate in cells having an activated ras pathway.

The term "attenuated vaccinia virus" or "modified vaccinia virus" means a vaccinia virus in which the gene product or products which prevents the activation of PKR is lacking, inhibited or mutated such that PKR activation is not blocked. Preferably, the E3L gene and/or the K3L gene is not transcribed. Such attenuated or modified vaccinia virus would not be able to replicate in normal cells that do not have an activated ras pathway, however, it would be able to infect and replicate in cells having an activated ras pathway.

The term "attenuated influenza virus" or "modified influenza virus" means an influenza virus in which the gene product or products which prevents the activation of PKR is lacking, inhibited or mutated such that PKR activation is not blocked. Preferably, the NS1 gene is not transcribed. Such attenuated or modified influenza virus would not be able to replicate in normal cells that do not have an activated ras pathway, however, it would be able to infect and replicate in cells having an activated ras pathway.

Methods

The present invention provides a method of detecting adventitious agents in a composition comprising microorganisms. An embodiment of the method is demonstrated in Example 1. Thus, to determine if an adventitious agent is present in a reovirus preparation, a plasmid that encodes a ribozyme, Rz-553 (Shahi et al., 2001), is constructed. Rz-553 is a "hammerhead" ribozyme consisting of a catalytic region flanked by two eight-nucleotide sequences that hybridize to the S1 segment of the reovirus genome. S1 codes for the protein σ1, which binds to the reovirus receptor on the cell. Therefore, cleavage of S1 RNA leads to reduced infectivity of any resultant virus. Also constructed is a plasmid encoding a mutant of Rz-553 in which a single nucleotide in the catalytic region is mutated (G to U). The mutant is known to be completely inactive.

The plasmids are introduced into COS-1 cells, and the transfected cells are exposed to an aliquot of the reovirus preparation being tested. Mock-infected cells are used as a control. As expected, cells expressing the mutant ribozyme had extensive CPE. However, cells expressing Rz-553 also show moderate CPE when compared to the mock-infected cells. Therefore, the reovirus preparation contains a non-reovirus agent that caused the CPE on COS-1 cells.

Any ribozyme capable of cleaving the target RNA sequence of a microorganism to inhibit replication or infection of the microorganism is useful in the present invention. The target sequence may be, for example, RNAs encoding structural proteins (particularly outer coat proteins), proteins of the replication machinery, or proteins important for cellular entry, such as the receptor protein. Methods for constructing sequence-specific ribozymes are well known in the art. For example, U.S. Pat. No. 5,254,678 describes the hammerhead ribozymes, which have a central catalytic region flanked by two hybridization regions. Upon hybridizing to the preselected target sequence through the hybridization regions, the catalytic region forms a secondary structure that facilitates cleavage, and cleaves the target sequence. Although this patent describes ribozymes in which at least one hybridization region has a minimum of nine hybridizing nucleotides, such minimal length is not required in the present invention. In the present invention, each hybridization region may contain six, seven, eight or more hybridizing nucleotides.

U.S. Pat. No. 6,307,041 describes derivatives of hammerhead ribozymes, including the circular, hairpin, circular/hairpin, lariat and hairpin-lariat forms of hammerhead ribozymes. These ribozymes have increased specific activity and different co-factor requirement, and may also be used in the present invention. Other examples include the hairpin ribozymes as described in, for example, U.S. Pat. Nos. 5,631,359 and 5,631,115.

All these ribozymes contain at least one hybridization region and a catalytic region. The hybridization region is designed according to the target sequence. The catalytic region can be derived from, for example, a hammerhead ribozyme (U.S. Pat. No. 5,254,678), a hairpin ribozyme (European Application No. 89 117 424), a hepatitis delta ribozyme (WO 91/04319 and WO 91/04324), an RNase P ribozyme (U.S. Pat. No. 5,168,053), a group I intron (U.S. Pat. No. 4,987,071), or a group II intron (Pyle, 1993).

It is also contemplated that more than one ribozyme can be combined in the present invention. For example, multiple ribozymes recognizing different regions of the same RNA can be combined. Alternatively and preferably, ribozymes specific for different RNAs of the same microorganism can be used together to increase the efficiency of inactivation of the microorganism. When multiple ribozymes are used, they can be encoded in the same expression vector or separately encoded.

The present invention may be used to detect the presence of adventitious agents in any microbial preparation. It should be noted that while ribozymes cleave RNA only, the application of the present invention is not limited to microorganisms with an RNA genome. Microorganisms with a DNA genome necessarily need to replicate through an RNA transcript, and/or synthesize proteins through an RNA transcript, as part of the infection process. Even prions need an RNA transcript to replicate and infect. Therefore, replication and infection of any microorganism can be inhibited by a ribozyme that specifically cleaves the microbial RNA transcript/genome.

The microorganism of the present invention is preferably a virus and more preferably an oncolytic virus. An oncolytic virus can selectively infect and kill neoplastic cells, thus is useful in virus therapy. In addition to reovirus, these viruses include, but are not limited to, modified adenovirus, modified HSV, modified vaccinia virus, modified parapoxvirus orf virus, modified influenza virus, p53-expressing viruses, the ONYX-015 virus, the Delta24 virus, vesicular stomatitis virus, the herpes simplex virus 1 mutant which is defective in hrR3, Newcastle disease virus, encephalitis virus, herpes zoster virus, hepatitis virus, influenza virus, varicella virus, and measles virus.

Adenovirus, HSV, vaccinia virus, and parapoxvirus orf virus are viruses which have developed a mechanism to overcome the double stranded RNA kinase (PKR). Normally, when virus enters a cell, PKR is activated and blocks protein synthesis, and the virus can not replicate in this cell. However, adenovirus makes a large amount of a small RNA, VA1 RNA.

VA1 RNA has extensive secondary structures and binds to PKR in competition with the double stranded RNA (dsRNA) which normally activates PKR. Since it requires a minimum length of dsRNA to activate PKR, VA1 RNA does not activate PKR. Instead, it sequesters PKR by virtue of its large amount. Consequently, protein synthesis is not blocked and adenovirus can replicate in the cell. It should be noted, however, that although the protein synthesis machinery is not blocked, host cell protein synthesis is inhibited by the virus to facilitate viral protein synthesis.

Vaccinia virus encodes two gene products, K3L and E3L, which down-regulate PKR with different mechanisms. The K3L gene product has limited homology with the N-terminal region of eIF-2α, the natural substrate of PKR, and may act as a pseudosubstrate for PKR. The E3L gene product is a dsRNA-binding protein and apparently functions by sequestering activator dsRNAs.

Similarly, herpes simplex virus (HSV) gene $_\gamma$34.5 encodes the gene product infected-cell protein 34.5 (ICP34.5) that can prevent the antiviral effects exerted by PKR. The parapoxvirus orf virus encodes the gene OV20.0L that is involved in blocking PKR activity. Thus, these viruses can successfully infect cells without being inhibited by PKR.

In the modified adenovirus, modified HSV, modified vaccinia virus, or modified parapoxvirus orf virus, the viral anti-PKR mechanism has been mutated or otherwise inactivated. Therefore, these modified viruses are not capable of replicating in normal cells which have normal PKR function. Ras-activated neoplastic cells, however, are not subject to protein synthesis inhibition by PKR, because ras inactivates PKR. These cells are therefore susceptible to infection by the modified adenovirus, modified HSV, modified vaccinia virus, or modified parapoxvirus orf virus.

The viruses can be modified or mutated according to the known structure-function relationship of the viral PKR inhibitors. For example, since the amino terminal region of E3 protein of the vaccinia virus interacts with the carboxy-terminal region domain of PKR, deletion or point mutation of this domain prevents anti-PKR function (Chang et al., 1992, 1993, 1995; Sharp et al., 1998; Romano et al., 1998). The K3L gene of vaccinia virus encodes pK3, a pseudosubstrate of PKR. There is a loss-of-function mutation within K3L. By either truncating or by placing point mutations within the C-terminal portion of K3L protein, homologous to residues 79 to 83 in eIF-2α abolish PKR inhibitory activity (Kawagishi-Kobayashi et al., 1997).

The modified HSV include, but are limited to, R3616 (both copies of the $_\gamma$34.5 gene have been deleted), R4009 (two stop codons have been inserted in the $_\gamma$34.5 gene), and G207 (mutated in the ribonucleotide reductase and the $_\gamma$34.5 genes) (Andreansky et al., 1996). These modified viruses have been used in brain tumor therapy, and it has been recently shown that R3616 preferentially infects ras-activated cells (Farassati et al., 2001).

Similarly, the delNS1 virus (Bergmann et al., 2001) is a genetically engineered influenza A virus that can selectively replicate in ras-activated neoplastic cells. The NS1 protein of influenza virus is a virulence factor that overcomes the PKR-mediated antiviral response by the host. NS1 is knocked out in the delNS1 virus, which fails to infect normal cells, presumably due to PKR-mediated inhibition, but replicates successfully in ras-activated neoplastic cells. Therefore, a modified influenza virus in which NS1 is modified or mutated, such as the delNS1 virus, is also useful in the present invention.

Other oncolytic viruses include the viruses which selectively kill neoplastic cells by carrying a tumor suppressor gene. For example, p53 is a cellular tumor suppressor which inhibits uncontrolled proliferation of normal cells. However, approximate half of all tumors have a functionally impaired p53 and proliferate in an uncontrolled manner. Therefore, a virus which expresses the wild type p53 gene can selectively kill the neoplastic cells which become neoplastic due to inactivation of the p53 gene product. Such a virus has been constructed and shown to induce apoptosis in cancer cells that express mutant p53 (Blagosklonny et al., 1996).

Adenoviruses carrying the E2 gene have also been developed (WO 02/095042). The E2 gene encodes the E2 protein, which inhibits oncogene expression and induces cellular senescence. Therefore, adenoviruses expressing the E2 gene can be used in gene therapy, particularly for cancer patients in the terminal stage.

A similar approach involves viral inhibitors of tumor suppressors. For example, certain adenovirus, SV40 and human papilloma virus include proteins that inactivate p53, thereby allowing their own replication (Nemunaitis 1999). For adenovirus serotype 5, this protein is a 55 Kd protein encoded by the E1B region. If the E1B region encoding this 55 kd protein is deleted, as in the ONYX-015 virus (Bischoff et al, 1996; Heise et al., 2000; WO 94/18992), the 55 kd p53 inhibitor is no longer present. As a result, when ONYX-015 enters a normal cell, p53 functions to suppress cell proliferation as well as viral replication, which relies on the cellular proliferative machinery. Therefore, ONYX-015 does not replicate in normal cells. On the other hand, in neoplastic cells with disrupted p53 function, ONYX-015 can replicate and eventually cause the cell to die. Accordingly, this virus can be used to selectively infect and kill p53-deficient neoplastic cells. A person of ordinary skill in the art can also mutate and disrupt the p53 inhibitor gene in adenovirus 5 or other viruses according to established techniques.

Another example is the Delta24 virus which is a mutant adenovirus carrying a 24 base pair deletion in the E1A region (Fueyo et al., 2000). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

Yet other oncolytic viruses include the interferon sensitive viruses. Vesicular stomatitis virus (VSV) selectively kills neoplastic cells in the presence of interferon. Interferons are circulating factors which bind to cell surface receptors which ultimately lead to both an antiviral response and an induction of growth inhibitory and/or apoptotic signals in the target cells. Although interferons can theoretically be used to inhibit proliferation of tumor cells, this attempt has not been very successful because of tumor-specific mutations of members of the interferon pathway.

However, by disrupting the interferon pathway to avoid growth inhibition exerted by interferon, tumor cells may simultaneously compromise their anti-viral response. Indeed, it has been shown that VSV, an enveloped, negative-sense RNA virus rapidly replicated in and killed a variety of human tumor cell lines in the presence of interferon, while normal human primary cell cultures were apparently protected by interferon. An intratumoral injection of VSV also reduced tumor burden of nude mice bearing subcutaneous human melanoma xenografts (Stojdl et al., 2000).

Other interferon-sensitive viruses (WO 99/18799), namely viruses which do not replicate in a normal cell in the presence of interferons, can be identified by growing a culture of normal cells, contacting the culture with the virus of interest in the presence of varying concentrations of interferons, then determining the percentage of cell killing after a period of incubation. Preferably, less than 20% normal cells is killed and more preferably, less than 10% is killed.

It is also possible to take advantage of the fact that some neoplastic cells express high levels of an enzyme and construct a virus which is dependent on this enzyme. For example, ribonucleotide reductase is abundant in liver metastases but scarce in normal liver. Therefore, a herpes simplex virus 1 (HSV-1) mutant which is defective in ribonucleotide reductase expression, hrR3, was shown to replicate in colon carcinoma cells but not normal liver cells (Yoon et al., 2000).

In addition to the viruses discussed above, a variety of other viruses have been associated with tumor killing, although the underlying mechanism is not always clear. Newcastle disease virus (NDV) replicates preferentially in malignant cells, and the most commonly used strain is 73-T (Reichard et al., 1992; Zorn et al, 1994; Bar-Eli et al, 1996).

Clinical antitumor activities wherein NDV reduced tumor burden after intratumor inoculation were also observed in a variety of tumors, including cervical, colorectal, pancreas, gastric, melanoma and renal cancer (WO 94/25627; Nemunaitis, 1999).

Moreover, encephalitis virus was shown to have an oncolytic effect in a mouse sarcoma tumor, but attenuation may be required to reduce its infectivity in normal cells. Tumor regression have been described in tumor patients infected with herpes zoster, hepatitis virus, influenza, varicella, or measles virus (for a review, see Nemunaitis, 1999). These viruses are thus also candidate oncolytic viruses.

It is contemplated that for the modified oncolytic viruses, in which a nucleic acid is modified to result in replication in tumor cells, the ribozyme can be designed to cleave the RNA that corresponds to the modified nucleic acid. The ribozyme can be introduced into the susceptible tumor cells to prepare the indicator cells. Since the ribozyme cleaves the modified RNA, which is responsible for infectivity in the tumor cells, no infection will occur unless there is an adventitious agent in the virus preparation.

Indicator Cells

The indicator cell should be prepared from a cell that is susceptible to infection of the microorganism to be validated. A construct encoding the appropriate ribozyme can be introduced into the susceptible cell by any method known in the art, such as calcium phosphate precipitation, liposome fusion, Lipofectin®, electroporation, and viral infection.

Both transient and stable introduction of the construct may be useful in the present invention. However, the indicator cells preferably express the ribozyme in a permanent manner. To this end, an expression vector encoding the ribozyme may be integrated into the genome of the cell or introduced as an episomal vector (such as a bovine papilloma virus vector). Typically, the expression vector contains a selectable marker, cells harboring the expression vectors are selected using the selectable marker and maintained under selection. Methods for constructing such vectors, transfection and selection are well known in the art (see, for example, Sambrook, 2001).

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
min=minute
µ=micromolar
mM=millimolar
M=molar
ml=milliliter
µl=microliter
mg=milligram
µg=microgram
FBS=fetal bovine serum
PBS=phosphate buffered saline
DMEM=Dulbecco's modified Eagle's medium
α-MEM=α-modified Eagle's medium
β-ME=β-mercaptoethanol
MOI=multiplicity of infection
PFU=plaque forming units
PKR=double-stranded RNA activated protein kinase
EGF=epidermal growth factor
PDGF=platelet derived growth factor
CPE=cytopathic effect Example 1

Testing a Reovirus Preparation

Reovirus is prepared and purified according to U.S. patent application Ser. No. 09/920,012. Briefly, human embryonic kidney 293 SF (293/SF) cells are cultured in 15 L spinner flasks and infected with reovirus at a multiplicity of infection of 0.5 when cell density reach $10^6$/ml. The culture is incubated until cell lysis begins, as evidenced by the culture media color change from red to orange due to the presence of phenol red in the media, or by a viable cell count under the microscope. At this point, the cells are harvested by centrifugation, resuspended and disrupted by freeze/thaw. The virus is then purified by a cesium chloride gradient.

COS-1 cells are used as an indicator cell line. Thus, COS-1 cells are grown to 60% confluency in 6-well plates and transfected with Rz-553 encoding DNA or control DNA (mutant S1-Rz-553) by using Lipofectin (GIBCO/BRL) as described in Shahi et al. (2001). pSVLacZ (Promega) is co-transfected in all the experiments to ensure uniform transfection efficiency. 12 hours later, the cells are washed once with fresh medium and infected with an aliquot of the reovirus preparation described above at an m.o.i. of 1 PFU/cell. Mock-infected cells are treated in the same manner without the reovirus preparation. 8 hours after infection, the cells are observed for cytopathic effects (CPE).

The mutant S1-Rz-553 transfected cells show extensive CPE as expected, since the mutant ribozyme does not inactivate reovirus and reovirus infection causes CPE on the infected cells. However, the Rz-553 transfected cells also display detectable CPE as compared to mock-infected cells. Since Rz-553 is known to inactivate reovirus, these results indicate that this reovirus preparation contains a non-reovirus agent that causes cytopathic effects on COS-1 cells.

I claim:
1. A method of validating a therapeutic composition comprising reovirus as having no detectable adventitious agent, the method comprising:
   (a) providing a therapeutic composition in need of validation, the therapeutic composition comprising a reovirus and suspected of further comprising an adventitious agent, wherein the adventitious agent is not a reovirus;

(b) providing a population of indicator cells that express a ribozyme, wherein the ribozyme is capable of specifically cleaving the genome of the reovirus;

(c) contacting the indicator cells with the therapeutic composition under conditions that allow for cleavage of the genome of the reovirus by the ribozyme; and (d) determining the effect of any adventitious agent in the therapeutic composition by detecting the presence or absence of a pathogenic effect on the indicator cells contacted with the therapeutic composition, wherein the presence of a pathogenic effect indicates the presence of an adventitious agent in the therapeutic composition; and (e) validating the therapeutic composition as having no detectable adventitious agent in the absence of a pathogenic effect.

2. The method of claim 1, wherein the indicator cells express the ribozyme from a gene that is integrated into the genome of the cells.

3. The method of claim 1, wherein the ribozyme is capable of specifically cleaving the s1 RNA of the reovirus.

4. The method of claim 1, wherein the ribozyme is Rz-553 or Rz-984.

5. The method of claim 1, wherein the reovirus is a mammalian reovirus or a human reovirus.

6. The method of claim 1, wherein the reovirus is a serotype 3 reovirus.

7. The method of claim 1, wherein the reovirus is a recombinant reovirus.

8. The method of claim 1, wherein the population of indicator cells comprises human cells.

9. The method of claim 1, wherein the adventitious agent is an infectious agent, other than reovirus, which is capable of infecting the indicator cell.

10. The method of claim 1, wherein the reovirus is prepared using human embryonic kidney cells.

* * * * *